United States Patent [19]

Vermess et al.

[11] 4,404,182

[45] Sep. 13, 1983

[54] ETHIODIZED OIL EMULSION FOR INTRAVENOUS HEPATOGRAPHY

[75] Inventors: Michael Vermess, Potomac; Dulal C. Chatterji, Germantown; George J. Grimes, Jr., Laurel; Joseph F. Gallelli, Bethesda, all of Md.

[73] Assignee: The United States of America as represented by the Department of Health and Human Services, Washington, D.C.

[21] Appl. No.: 110,293

[22] Filed: Jan. 8, 1980

[51] Int. Cl.³ ............................................. A61K 49/04
[52] U.S. Cl. ....................................................... 424/5
[58] Field of Search ............................................ 424/5

[56] References Cited

U.S. PATENT DOCUMENTS 3,356,575  12/1967  Arbaeus et al. ......................... 424/5

OTHER PUBLICATIONS

Journal of Pharmaceutical Sciences, vol. 68, No. 1, Jan. 1979–Grimes et al.
J. Comput. Assist. to Mdgr., vol. 3, No. 1, 1979, Vermess et al., pp. 25–31.

*Primary Examiner*—Frederick E. Waddell
*Attorney, Agent, or Firm*—John S. Roberts, Jr.

[57] ABSTRACT

The present invention is directed towards the examination of formulations and evaluations of ethiodized oil emulsions. It is also concerned with formulations of ethiodized oil emulsified with lecithin which show about 30–35% of oil particles in the range 2–3 microns. A dosage utilized for animals, such as rabbits and monkeys for this ethiodized emulsion is 0.1–0.5 ml/kg utilizing computerized tomography, with a preferred dosage of 0.2 ml/kg for computerized tomography, and a dosage of 2 ml/kg for conventional X-rays.

4 Claims, 3 Drawing Figures

ETHIODIZED OIL EMULSION FOR INTRAVENOUS HEPATOGRAPHY

The present invention is directed towards the examination of formulations and evaluations of ethiodized oil emulsions. It is also concerned with formulations of ethiodized oil emulsified with lecithin which show about 30-35% of oil particles in the range 2-3 microns. A dosage utilized for animals, such as rabbits and monkeys, for this ethiodized emulsion is 0.1-0.5 ml/kg utilizing computerized tomography, with a preferred dosage of 0.2 ml/kg for computerized tomography, and a dosage of 2 ml/kg for conventional X-rays.

In recent medical history there have been numerous attempts for opacify the liver and spleen by intravenously administered contrast or opacifying material. The iodinated oil emulsion developed in the present invention can be injected intravenously to increase selectively the X-ray attenuation of liver and spleen in experimental animals and has potential clinical application in the diagnosis of liver tumors. A low amount or dosage is of key importance. Thus, in the present formulations, if one uses the computerized tomography, a dosage as low as 0.1 ml/kg can be achieved and using ordinary conventional X-ray the dosage is 2 ml/kg.

PRIOR ART STATEMENT

The following literature references and patents are believed to be of interest in connection with this invention.

Grimes et al, "Formulation and Evaluation of Ethiodized Oil Emulsion for Intravenous Hepatography," *Journal of Pharmaceutical Sciences*, Vol. 68, No. 1, January 1979, pages 52-56.

Vermess et al, "Development and Experimental Evaluation of a Contrast Medium for Computed Tomographic Examination of the Liver and Spleen," *J. Comput. Assist. Tomogr.*, Vol. 3, No. 1, February 1979, pages 25-31.

U.S. Pat. No. 3,937,800 Dure-Smith et al—The micron size is taught in an X-ray contrast method referring to tantalum dispersed in a liquid vehicle. The abstract reads that preferably the range is about 1 to 5 microns and the utilization as an opaque agent is for bronchography.

U.S. Pat. No. 4,120,946 Queuille et al—This patent shows "colloidal barium sulfate" and Hackh's Chemical Dictionary, 4th Edition, McGraw-Hill, 1969, gives colloidal particle size in an area of about 1-100 microns. A preferred opacification of the digestive tract is one part of approximately 0.7% polyacrylamide gel to 1.4 parts of colloidal barium sulfate.

It has been demonstrated that there is a great need to reduce toxic and disturbing reactions such as fever, chill, anorexia, nausea, and vomiting experienced by the patient injected with an opacifier. While work has been dones with oil emulsions as opacifiers, development of an iodinated oil emulsion which can be injected intravenously to increase selectively the X-ray attenuation of liver and spleen in experimental animals had not been achieved previously and the development of a suitable emulsifier, particularly one which can be utilized in a small amount, had heretofore not been realized.

It has been recognized that various tissues absorb oil globules of different sizes. However, in the prior art it had not been recognized that the size distribution of emulsified iodinated oil globules is of significant importance in achieving the desired degree of liver opacification. Development of the globule size distribution is a significant achievement of the present invention and makes possible more effective use of the ethiodized oil emulsion for the best opacification of the liver. Low effective dosages give excellent opacification when utilized with computerized tomography.

Another achievement of the present invention is the preparation of purified lechithin from soy lecithin for use as the emulsifying agent by extracting in alcohol. The amount of the alcoholic extract used to make 100 ml of emulsion contains only 450 mg. of extracted solids of lechithin (0.45%). The range may be 0.40 to 2.0%, and is still highly effective. Heretofore, emulsifiers have been utilized at a level of 3% or usually greater. The low level of emulsifier is particularly desirable and it avoids the use of potentially toxic synthetic surfactants.

In regard to the preferred size distribution the best results were achieved with an emulsion wherein a great percentile of the oil particles are in the 2-3 micron area. Such a percentile may be in the area of 32-35%.

TABLE 1

Formulation of Emulsions

| Emulsion | Emulsifier/100 ml | Mix Speed[a] | Comments |
|---|---|---|---|
| III | Polysorbate 80, 4.5 g and sorbitan monooleate, 1.5 g | Medium | Opacified spleen but did not significantly opacify liver; average globule size smallest of all emulsions and least effective |
| IV | Polysorbate 80, 2.25 g, and sorbitan monooleate, 0.75 g | Medium high | Opacified liver well but not as well as V and VI |
| V | Alcoholic extract of lecithin[b], 10 ml | Medium high | Most effective of all emulsions in liver opacification, reproducibility, and clarity |
| VI | Lecithin in ethanol, 3.0 g/10 ml | Medium high | Opacified as well as V but not as reproducible |
| IIb | Lecithin, 3 g, and polyoxyl 40 stearate, 1.2 g | | Unavailable commercial product, used for comparison purposes |

[a]The mix time was 3 min. for Emulsions II-VI.
[b]Extract from 2.5 g of lecithin, representing 0.45 g of extracted solids Ethiodized oil of chemically pure grade is preferably obtained from Savage Laboratories, Houston, Tex. 77036, and the lecithin is utilized in an alcoholic extract in Emulsion V, alcoholic extract of lecithin, 10 ml. In Emulsion VI the lecithin is utilized in ethanol, 3.0 g/10 ml.

Emulsion III (Table 1) was prepared and the emulsion, when examined under a microscope, revealed that most of the globules were around 1 micron in diameter; a few were between 1.5-2.0 microns, and very few were above 2 microns. Emulsion III, at a dose of 2.0 ml/kg, was tested in rabbits by the conventional radiographic technique and showed only minimal opacification of the liver. An emulsion with a globule size smaller than that of Emulsion III also opacified the liver poorly. Therefore, an emulsion with a larger globule size was investigated.

Emulsion IV was made with the same polysorbate 80-sorbitan monooleate emulsifier combination as Emulsion III, but a smaller amount of emulsifier was used (see Table 1). On microscopic observation, Emulsion IV showed a good number of globules in the 1.5-2.0 micron range and very few above the 3-5 micron range. Although Emulsion IV opacified the liver in rabbits, it was somewhat less effective than IIb. Thus, this emulsion showed promise and probably could have been improved further by changing the emulsifier concentration to increase the globule size.

The use of lecithin was investigated. To eliminate the major problem of spongy masses observed with refined soy lecithin, the lecithin was purified further by extraction in ethanol. When the alcoholic extract was used along with the addition of enough alcohol to make the final alcohol concentration 10% (v/v) in the emulsion, it no longer contained spongy masses and appeared clean under the microscope. Therefore, variations of the formulation were examined by changing the emulsifier concentration or stirring speed, which resulted in the preparation of Emulsion V (Table 1).

Emulsion V, at doses of 2.0 ml/kg for conventional X-ray and 0.2 ml/kg for computerized tomography, produced denser liver scans than Emulsions III and IV. Microscopic observation of Emulsion V revealed that the globule sizes were generally larger than those in Emulsions III and IV, and a large number of globules were in the 2-micron range. A further increase in the size of the globules in Emulsion V (obtained by changing the stirring speed or homogenizing time) resulted in an emulsion that gave unsatisfactory liver scans.

Since Emulsion V was made using an alcoholic extract of soy lecithin, it was thought that a purer commercial extract of lecithin, used without further processing, would give a more reproducible emulsion. Therefore, various alcohol-soluble lecithins containing various amounts of phosphatidyl choline were evaluated. Phosphatidyl choline 80% was studied most because of its high alcohol solubility. Emulsion VI (Table 1), prepared with 3% (w/v) phosphatidyl choline, resulted in globule sizes that were larger than those of Emulsion V, but a good number of globules were in the 2-2.5 micron range. However, relatively fewer globules were below 1.5 microns and more globules were larger than 3 microns, compared to Emulsions III-V.

The potency of Emulsion VI in opacifying the liver was comparable to that of Emulsion V. However, during the preparation of Emulsion VI, the temperature of the oil and water phases had to be very strictly adhered to (otherwise the primary emulsion gelled), and the procedure did not prove to be reproducible. Furthermore, the concentration of the emulsifier in Emulsion VI was much higher than that of Emulsion V (3% compared to 0.45% in Emulsion V), and attempts to reduce it resulted in an even poorer emulsion. Therefore, Emulsion V was chosen for toxicity and clinical studies.

TABLE 2

| | Globule Size Distribution of Emulsions | | | | | | | | | |
|---|---|---|---|---|---|---|---|---|---|---|
| | Emulsion III | | Emulsion IV | | Emulsion V | | Emulsion VI | | Emulsion IIb | |
| Size Range (micron) | Number % | Volume % | Number % | Volume % | Number % | Volume % | Number % | Volume % | Number % | Volume % |
| 0.75-1.0 | 59.77 | 28.1 | 41.67 | 10.73 | 46.94 | 6.03 | 31.09 | 2.62 | 31.43 | 2.31 |
| 1.0-1.5 | 33.92 | 45.1 | 34.61 | 25.21 | 24.9 | 9.05 | 28.75 | 6.86 | 26.96 | 5.61 |
| 1.5-2.0 | 5.69 | 21.4 | 18.08 | 37.24 | 11.91 | 12.24 | 17.2 | 11.6 | 15.6 | 9.2 |
| 2.0-2.5 | 0.5 | 3.8 | 2.2 | 9.6 | 7.0 | 15.5 | 9.8 | 14.3 | 10.8 | 13.7 |
| 2.5-3.0 | 0.1 | 1.6 | 1.4 | 11.2 | 4.5 | 18.2 | 6.3 | 16.7 | 6.2 | 14.5 |
| 3.0-4.0 | — | — | 0.3 | 5.1 | 3.4 | 28.4 | 5.4 | 29.3 | 6.9 | 32.3 |
| 4.0-5.0 | — | — | 0.03 | 1.1 | 0.5 | 9.0 | 1.4 | 16.2 | 1.9 | 19.6 |
| 5.0-7.0 | — | — | — | — | 0.03 | 1.6 | 0.08 | 2.4 | 0.12 | 2.7 |
| Relative density of liver scans[a] | <40 | | 47 | | 57 | | 56 | | 50 | |

[a] In rabbits at a dose of 0.5 ml/kg using computerized tomography; density of control animal was 32. Numbers expressed in EMI Units (EU) on the 500 scale.

Correlation of Globule Size and Density of Liver Scans

Table 2 above shows the globule size distribution, both by number and volume (mass), of various emulsions along with the results of their in vivo testing. Since only the volume of the oil absorbed in the liver affects the degree of opacification, the density of liver scans was correlated with the volume distribution and not the number distribution of the globules. The size range of less than 1.5 microns was ruled out completely because Emulsion III, which contained the highest amount of oil in this range, was relatively inactive. Likewise, the size range of 1.5-2.0 microns was ruled out because, although Emulsion IV contained 37.2% oil of this size, it opacified the liver poorly as compared to Emulsions V, VI, and IIb, which all contained far less oil in this range. Size above 3.0 microns was also ruled out because IIb, which contained the highest amount of oil in this range, opacified the liver less than Emulsions V and VI.

Opacification of the liver was, therefore, related to the amount of the oil in the 2.0-3.0 micron range. Also, there was a direct rank-order correlation between the volume of the oil in the 2.0-3.0 micron size range and the density of the liver scans (Table 2). Another indication of the importance of the 2-3 micron size range was observed when Emulsion IV, after being stored at room temperature for several months, opacified the liver better than when freshly prepared and had a potency comparable to Emulsions V and VI. A globule size analysis of the aged Emulsion IV showed that globules had generally increased in size and that 32% (v/v) of the oil was now in the 2.0-3.0 micron range (compared to 20.7% in fresh Emulsion IV, Table 2). The increased potency of the aged Emulsion IV was due to an increase in the volume of the oil in the 2.0-3.0 micron range.

A correlation of the density of the liver scans with the volume fraction of the oil in a particular size range has been shown to be very important. Therefore, to prepare the best emulsion, the formulator should attempt to prepare emulsions such that most of the oil globules are in the specific size range needed, rather than homogenizing the emulsion to a globule size less the 1 micron. As seen from Table 2, only about a third of the oil in Emulsion V was in the 2.0-3.0 micron range. Since the lever takes up oil globules preferentially between 2.0 and 3.0 microns, if an emulsion could be prepared in which all the oil was in this range, it would be possible to reduce the emulsion dose to perhaps one-third and still deposit the same amount of iodinated oil in the liver. Such a preparation would have an added advantage of sparing other tissues from unnecessary exposure to iodinated oil.

The results of the present investigation indicate that at least one organ, the liver, has preference regarding the size of the oil globules it absorbs.

EXAMPLE 1

Figure 2:
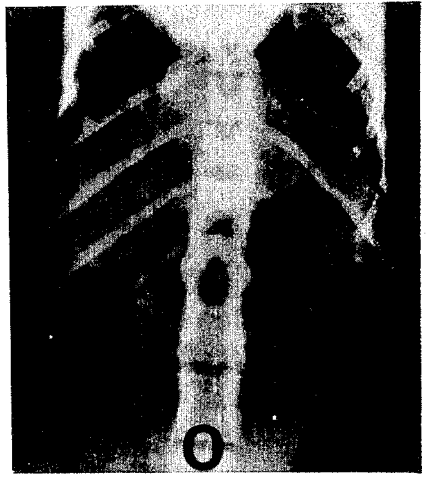
FIGS. 1, 2, and 3 show radiographs of rhesus monkey livers before (FIG. 1), 1 hour (FIG. 2), and 48 hours (FIG. 3) after the intravenous injection of 2 ml of Emulsion V/kg. A marked increase is indicated in the density of liver and spleen after 1 hour and almost complete clearance of the contrast material 48 hours after the injection.
Figure 1:
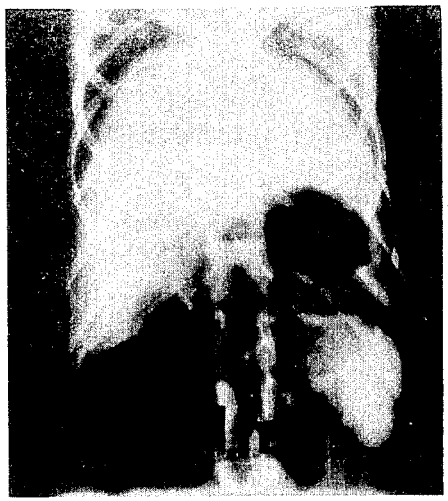
Figure 3:
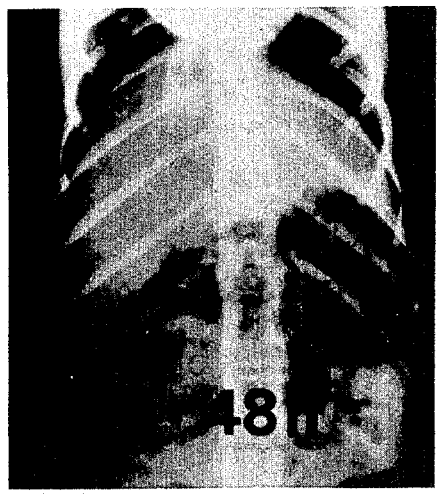

Materials and Equipment—Water for injection, ethiodized oil [Ethiodol, iodinated ester of poppyseed oil, iodine content 37% (w/v), is used for lymphography; Savage Laboratories, Houston Tex. as 77036], polysorbate 80 (Atlas Chemical Industries, Wilmington, Del.), sorbitan monooleate (Atlas Chemical Industries, Wilmington, Del.), phosphatidyl choline (Phospholipon-80, containing 80% phosphatidyl choline, American Lecithin Company, Atlanta, Ga.), and particle-free electrolyte solution (Isoton II, conducting fluid for Coulter Counter measurements, Coulter Diagnostics, Hialeah, Fla.) were used as received. All other chemicals were reagent grade.

An alcoholic extract of lecithin was prepared as follows. About 200 ml of absolute ethanol was added to 50 g of soy lecithin-refined (ICN Pharmaceuticals, Cleveland, Ohio), and the mixture was stirred for 20 min. and filtered through a fine muslin and then through a filter paper. The remaining slurry and filters were rinsed with enough alcohol to give a final volume of 200 ml of filtrate. When analyzed for solid content (by drying in a steam bath to constant weight), each milliliter of the extract was found to contain 45 mg of solids.

Emulsions were prepared using a homogenizer, and their globule size was evaluated using an electronic counter. Computerized tomographic scans for liver were performed with a computerized body scanner.

The ethiodized oil, Ethiodol, iodinated ester of poppyseed oil, iodine content 37% (w/v), Savage Laboratories, Houston, Tex., was the oil of choice in this development. Other non-toxic vegetable oils may be substituted therefor.

Preparation of Emulsions—In each emulsion, the contents of four 10-ml ampuls of ethiodized oil (total volume of 40 ml, 53 g) were emulsified and brought to a total volume of 100 ml. Thus, the emulsions contained 53% (w/v) of ethiodized oil, equivalent to approximately 0.2 g of iodine/ml of emulsion. Emulsions were prepared by dissolving water-soluble ingredients and emulsifiers in water and oil-soluble emulsifiers in oil. The alcoholic extract of lecithin, when required in the formulation, was also added to the oil phase.

Each phase was heated separately, with mechanical stirring, to 60°. The oil phase was then poured slowly into the stirring aqueous phase. Stirring was continued for 3 min. to form the primary oil-in-water emulsion. The volume of the mixture was adjusted to 100 ml with water, and the mixture was then poured into a 500-ml homogenizer flask and milled at specific speed settings (medium, medium high, or high) for a specified time. The rotor shaft of the homogenizer contained two sharp propeller blades, each 3 cm long and 1.5 cm apart at an angle of 30° to each other. The lower blade was fixed at the extreme end of the shaft and adjusted to 6 mm above the bottom surface of the homogenizing flask.

Sterile emulsions were prepared by passing each phase through sterile 0.22 micron filters into sterile flasks and carrying out the remaining procedures (as above) using the aseptic techniques and sterile equipment and supplies where needed. The emulsions were then aseptically transferred to sterile 50 ml multiple-dose vials, which were stoppered with sterile rubber closures and crimped with aluminum caps. The vials were stored at room and refrigeration (2°-6°) temperatures.

Experimental Evaluation In Vitro—Gross Observation: Each emulsion was periodically checked visually for sedimentation, viscosity changes, and redispersibility of layers.

Microscopic Observation: Approximately 0.5 ml of a well-shaken emulsion was diluted with 20 ml of distilled water and again mixed well.

One drop of this dilution was placed on a microscope slide and observed at X1125 magnification. A grid attachment (1.8 micron/grid square) in the ocular lens was used to measure globule size.

In general, a good emulsification resulted in a maximum number of globules in the 1-3 micron size range. Particular attention was given to the number of globules above 5 microns (diameter) or to any unusual or undissolved particles.

Electronic Counter Analysis: The electronic counter was used for quantitating the globule size of the emulsions. To prepare samples for analysis, the emulsions were diluted to a 1:40,000 concentration by first taking 50 $\mu$l of an emulsion and then diluting it with 2 ml of electrolyte solution. A 20-$\mu$l aliquot of this dilution was further diluted to 20 ml with electrolyte solution in a disposable, particle-free, plastic beaker. Counts were then performed using a 30 micron aperture tube and a 50-$\mu$l sampling volume, which generally contained from 80,000 to 100,000 globules above 0.75 micron in diameter.

The counter was calibrated with 2.02 micron mono-sized, polystyrene beads. Counts representing the number of globules above a specified diameter were obtained. The count between any size range was calculated by the difference between the cummulative counts above the extremes. The average volume of the globules in a given size range was calculated by the geometric mean of the extremes of the range. Globules below 0.75 micron in diameter were not considered in calculations or evaluation because they were thought to be unimportant in opacifying the liver and because the total volume of this range would not significantly contribute to error in the volume calculations of the larger globules (the contribution of $d^3$ factor decreases rapidly as diameter, d, decreases). Both the number and volume distribution of the oil globules in the emulsions were calculated.

A potential source of error with this counting procedure is as follows. During the counting, counts for globules larger than 2.0 microns decreased with time (in the diluted emulsion) whereas counts for particles around 1.0 and 1.5 microns remained relative constant. This result is contrary to the general behavior of emulsions, which, after dilution with saline solutions, usually give higher counts of larger globules, due to coalescence of smaller globules. No explanation is apparent for the unusual behavior of ethiodized oil emulsion diluted in electrolyte solution. To minimize this error, the counts were taken as quickly as possible after mixing, starting from the largest size (7 microns) and working down to the 1-micron level. All data presented are the average of at least three runs.

Experimental Evaluation In Vivo—The in vivo evaluation of the emulsions was performed in three stages. Not all emulsions were examined at all three stages; many were eliminated at the first- or second-stage level.

First-Stage Experiments: First-stage experiments were done with groups of four New Zealand White rabbits, 1.0–3.3 kg. Following the cannulation of an ear vein, the animals were lightly anesthetized with a 2% solution of thiamylal sodium. The initial dose was 1 ml/kg; additional small doses were administered as required to keep the animal under light anesthesia. A 2-ml/kg dose of the experimental emulsion was then injected through the same venipuncture, with the injection rate approximately 1 ml/min.

Prior to the intravenous injection of the emulsion, a preliminary abdominal radiograph was obtained on each animal. Following the completion of the injection, additional X-rays were obtained at 0.5, 1, 1.5, 2, and 3 hr. The increase of the opacity of the livers and spleens was then visually compared, and the effectiveness of the emulsion was evaluated on the basis of the comparison.

Second Stage Experiments: New Zealand White rabbits were again utilized in groups of four. The preliminary anesthesia was performed as in Stage I. Three of the four rabbits received 0.5 ml/kg of the test emulsions via the intravenous cannula, with the injection rate the same as in Stage I. One rabbit in the group was used as a control and injected with 0.5 ml of normal saline/kg. Following the injection, the animals were kept under light anesthesia for 1 hr and then sacrificed by rapid intravenous injection of thiamylal sodium until the cessation of respiration and heartbeat.

The dead animals were refrigerated for 2 hr, after which computerized tomographic scans of the livers and, occasionally, the spleens were obtained. The computerized tomographic scans were performed with a computerized body scanner utilizing the 25.4-cm scanning circle and 80-sec scanning time. The slice thickness of the scans was 13 mm, and the scans were performed at 1-cm distances. The number of slices necessary to obtain proper visualization of the liver parenchyma varied according to the size of the livers. The densities of the livers and, occasionally, the spleens were measured both visually on the measure mode and by the computer-generated mean attenuation value of a selected homogeneous area of the liver on the independent viewing console.

Third-Stage Experiments: These experiments were conducted on three female and two male normal rhesus monkeys, 3–6 kg. The animals were sedated and anesthetized. To prevent respiratory motion during the 80-sec exposure of the computerized tomographic scanning, the animals were intubated and connected to a respirator. Spontaneous respiration was eliminated by intravenous administration of 3 mg of tubocurarine chloride. Preliminary scans of the liver and, occasionally, the spleen were obtained utilizing the equipment and technique described in Stage II.

Following the preliminary scans, 0.2 ml of the experimental emulsion/kg was slowly injected (over approximately 1 min) into a peripheral vein. Thirty minutes after completion of the injection, the scans of the liver were repeated. In most experiments, the animals were also rescanned 60 min after the injection.

The density of the livers was measured on preliminary, 30-, and 60-min scans, as described in the Stage II experiments, both visually and by the computer-generated mean attenuation expressed in EMI Units (EU) on the 500 scale. The increases in the density of the livers after 30 and 60 min were compared to the preliminary scan and evaluated.

We claim:

1. A method of showing opacification in the liver and spleen of animals by injecting intravenously a dosage of emulsified ethiodized oil which contains about 30–35% of oil particles in the size range of 2–3 microns to increase selectively the X-ray attenuation of liver and spleen in experimental animals.

2. The method of claim 1 wherein the dosage range is 0.1 to 0.5 ml/kg of animal body weight for computerized tomography.

3. The method of claim 2 wherein the dosage is 0.2 ml/kg.

4. The method of claim 1 wherein the animals are selected from rabbits and monkeys.

* * * * *

UNITED STATES PATENT OFFICE
CERTIFICATE OF CORRECTION

Patent No. 4,404,182          Dated September 13, 1983

Inventor(s) Michael Vermess, Dulal C. Chatterji, George J. Grimes, Jr., and Joseph F. Gallelli It is certified that error appears in the above-identified patent and that said Letters Patent are hereby corrected as shown below:

Column 8, Claim 1, line 6, delete "experimental"

Signed and Sealed this

Twenty-sixth Day of March 1985

[SEAL]

Attest:

DONALD J. QUIGG

Attesting Officer    Acting Commissioner of Patents and Trademarks